US012637708B2

(12) United States Patent
Shen et al.

(10) Patent No.: US 12,637,708 B2
(45) Date of Patent: May 26, 2026

(54) METHOD AND APPARATUS FOR GENERATING DROPLET ARRAY ON MICROFLUIDIC CHIP

(71) Applicant: SHANGHAI JIAOTONG UNIVERSITY, Shanghai (CN)

(72) Inventors: Feng Shen, Shanghai (CN); Haijun Qu, Shanghai (CN); Weiyuan Lyu, Shanghai (CN); Yan Yu, Shanghai (CN)

(73) Assignee: SHANGHAI JIAOTONG UNIVERSITY, Shanghai (CN)

( * ) Notice: Subject to any disclaimer, the term of this patent is extended or adjusted under 35 U.S.C. 154(b) by 1123 days.

(21) Appl. No.: 17/635,218

(22) PCT Filed: Sep. 3, 2020

(86) PCT No.: PCT/CN2020/113313
§ 371 (c)(1),
(2) Date: Feb. 14, 2022

(87) PCT Pub. No.: WO2021/043224
PCT Pub. Date: Mar. 11, 2021

(65) Prior Publication Data
US 2022/0220548 A1 Jul. 14, 2022

(30) Foreign Application Priority Data

Sep. 6, 2019 (CN) .......................... 201910841256.8

(51) Int. Cl.
*B01L 7/00* (2006.01)
*B01D 15/08* (2006.01)
(Continued)

(52) U.S. Cl.
CPC .......... *C12Q 1/6851* (2013.01); *B01L 3/5027* (2013.01); *B01L 2300/161* (2013.01)

(58) Field of Classification Search
CPC ............ C12Q 1/6851; C12Q 2531/113; C12Q 2563/159; C12Q 2565/629; B01L 3/5027;
(Continued)

(56) References Cited

U.S. PATENT DOCUMENTS

2007/0144967 A1* 6/2007 Guenther .......... B01L 3/502753
95/260
2012/0028342 A1* 2/2012 Ismagilov ............. B01F 33/304
422/503
(Continued)

FOREIGN PATENT DOCUMENTS

CN 102836751 A * 12/2012
CN 104722342 A 6/2015
(Continued)

OTHER PUBLICATIONS

Xu, Peng, et al. "Cross-interface emulsification for generating size-tunable droplets." Analytical chemistry 88.6 (2016): 3171-3177. (Year: 2016).*
(Continued)

*Primary Examiner* — Jennifer Wecker
*Assistant Examiner* — Oyeleye Alexander Alabi
(74) *Attorney, Agent, or Firm* — NKL Law; Bin Lu; Allen Xue

(57) ABSTRACT

The present invention provides a method for generating a droplet array on a microfluidic chip, comprising the following steps: assembling an upper chip and a lower chip to an initial position, a fluid channel of the upper chip partially or completely covering a microporous array of the lower chip; injecting a solution into a chip, the solution being partially or fully filled in the microporous array of the lower chip; and relatively moving the upper chip and the lower chip to a liquid dividing position, the fluid channel of the upper chip and the microporous array of the lower chip being over-
(Continued)

lapped no longer, and the solution being dispersed into the microporous array to form a droplet array. A contact surface between the upper chip and the lower chip is hydrophobic, and the microporous array sufficiently separates the generated droplets physically, thereby avoiding cross-contamination. The present invention can effectively control the size and shape of the generated droplet.

15 Claims, 15 Drawing Sheets

Specification includes a Sequence Listing.

(51) Int. Cl.

| | |
|---|---|
| *B01F 33/302* | (2022.01) |
| *B01F 33/3033* | (2022.01) |
| *B01J 20/285* | (2006.01) |
| *B01J 20/287* | (2006.01) |
| *B01J 20/32* | (2006.01) |
| *B01L 3/00* | (2006.01) |
| *B01L 9/00* | (2006.01) |
| *B65G 47/80* | (2006.01) |
| *B82Y 20/00* | (2011.01) |
| *B82Y 30/00* | (2011.01) |
| *B82Y 40/00* | (2011.01) |
| *C08L 5/08* | (2006.01) |
| *C12M 1/34* | (2006.01) |
| *C12M 3/06* | (2006.01) |
| *C12N 1/14* | (2026.01) |
| *C12N 1/20* | (2026.01) |
| *C12Q 1/02* | (2006.01) |
| *C12Q 1/6806* | (2018.01) |
| *C12Q 1/6844* | (2018.01) |
| *C12Q 1/6848* | (2018.01) |
| *C12Q 1/6851* | (2018.01) |
| *C12Q 1/686* | (2018.01) |
| *G01K 1/14* | (2021.01) |
| *G01N 1/44* | (2006.01) |
| *G01N 15/10* | (2024.01) |
| *G01N 15/14* | (2024.01) |
| *G01N 15/1433* | (2024.01) |
| *G01N 21/01* | (2006.01) |
| *G01N 21/03* | (2006.01) |
| *G01N 21/29* | (2006.01) |
| *G01N 21/33* | (2006.01) |
| *G01N 21/65* | (2006.01) |
| *G01N 21/77* | (2006.01) |
| *G01N 27/07* | (2006.01) |
| *G01N 27/28* | (2006.01) |
| *G01N 27/416* | (2006.01) |
| *G01N 30/02* | (2006.01) |
| *G01N 30/60* | (2006.01) |
| *G01N 30/72* | (2006.01) |
| *G01N 31/12* | (2006.01) |
| *G01N 33/543* | (2006.01) |
| *G01N 33/557* | (2006.01) |
| *G01N 33/564* | (2006.01) |
| *G01N 33/574* | (2006.01) |
| *G01N 33/58* | (2006.01) |
| *G01N 33/68* | (2006.01) |
| *G01N 35/00* | (2006.01) |
| *H05B 45/10* | (2020.01) |

(58) Field of Classification Search
CPC ....... B01L 2300/161; B01L 2200/0605; B01L 2200/0673; B01L 2300/0864; B01L 2300/0887; B01L 2400/065; B01L 3/502738
See application file for complete search history.

(56) References Cited

U.S. PATENT DOCUMENTS

| | | | | |
|---|---|---|---|---|
| 2015/0247190 A1* | 9/2015 | Ismagilov | ........... | C12Q 1/6851 435/6.15 |
| 2016/0288121 A1* | 10/2016 | Ismagilov | ............. | C12Q 1/025 |
| 2019/0118177 A1* | 4/2019 | Ismagilov | ........... | C12Q 1/6855 |

FOREIGN PATENT DOCUMENTS

| | | | | | |
|---|---|---|---|---|---|
| CN | 106755345 A | * | 5/2017 | ......... | C12Q 1/6851 |
| CN | 108837718 A | | 11/2018 | | |
| CN | 109046484 A | | 12/2018 | | |
| CN | 110643483 A | | 1/2020 | | |

OTHER PUBLICATIONS

Helen Song et al., "Reactions in Droplets in Microfluidic Channels", Angewandte Chemie, Ed. 2006, 45, p. 7336-7356.

* cited by examiner fluid channel inlet outlet microwell array expansion channel nucleic acid concentration ☐ stilla ■ ; system in the present invention

METHOD AND APPARATUS FOR GENERATING DROPLET ARRAY ON MICROFLUIDIC CHIP

TECHNICAL FIELD

The present invention relates to droplet generation, in particular to a method for generating droplet array on microfluidic chip and an apparatus for the same.

BACKGROUND TECHNOLOGY

Droplets (droplet) are widely used in physics, chemistry, biology and medicine. A large number of (usually more than 100) droplet arrays show good specificity in gene, protein and cell analysis, among which digital PCR gene magnification is a technology for accurate quantification of target gene based on a large number of independent microdroplets. By dispersing the reaction solution into picoliters or nano-liters microdroplets or reaction microwells, each micro-droplet or microwell contains at most one copy of the target gene. For example, some microdroplets or microwells contain a target gene while other micro-droplets or microwells do not contain the target gene. By specific amplification of the target gene in micro-droplets or microwells, a detectable signal is produced, such as a fluorescent signal. By counting the proportion of microdroplets with signal enhancement to the total number of droplets (or the proportion of microdroplets without signal enhancement to the total number of droplets), the initial concentration of the target gene can be accurately calculated according to statistical calcu-lation methods such as Poisson distribution.

At present, the methods of digital PCR quantification are mainly sorted into the method of flow-generated-microdrop-let and the method of reactive-microwells chips. Both meth-ods achieve the purpose of digital PCR by dispersing the reaction solution into a large number of micro reaction cells.

In the method of flow-generated-microdroplet, the aque-ous solution is cut off with organic liquid to generate a series of droplets, mainly via the special design of microfluidic fluid channels. Refer to Angew. Chem. Int. Ed. 2006, 45, 73336-7356 for the description of the said method. One of the representatives of the flow method is cross-flowing droplet formation. Through the flow of the organic phase and the aqueous phase at an angle to each other (T-type or Y-type), the method uses shear force to stretch the aqueous phase and finally generates droplets. Another representative method is flow focusing droplet formation. This method generates droplets through the non-parallel flow of the organic phase and the aqueous phase passing through a limited, narrow region. Another method is co-flowing drop-let generation. This method is to enclose the dispersed phase (e.g. water phase) channel in the continuous phase (e.g. organic phase) channel. At the end of the dispersed phase channel, the fluid is stretched until the shear force breaks it to form droplets. These methods described above have been commercialized in a number of products, a representative one being the droplet-based digital PCR system (ddPCR) from BioRad. The droplet-based digital PCR system (ddPCR) from BioRad has a set of chips for droplet gen-eration which can generate tens of thousands of nanoscale microdroplets relatively quickly. The microdroplets are amplified in a thermal cycler, and the fluorescence of the microdroplets is detected by a liquid fluorescence detection system, which is similar to flow detection.

The chip method mainly forms microwells or microreac-tion-cells on the microfluidic chip, and then disperses the aqueous solution of the dispersed phase into the microwells or microreaction-cells, so that the water phase in the microwells forms relatively independent microdroplets. One of the representative is QuantStudio 3D digital PCR system from Thermo Fisher. Thermo Fisher's system has a micro-fluidic chip containing tens of thousands of reactive microw-ells, which disperses the reaction solution into these microwells and then covers these microwells with an organic phase (oil phase) to form independent reactive microwells.

Slipchip is a microfluidic chip. A large number of microw-ells are prepared on the lower surface of the upper sub-chip and the upper surface of the lower sub-chip. In the initial position, the upper and lower sub-chips are assembled together, and the microwells of the upper and lower sub-chips are partially superimposed to form a connected fluid channel. After the solution is injected into the chip, the upper and lower sub-chips are relatively slid, and the microwells are no longer partially superimposed on each other, thereby generating a large number of droplets. This method requires a large number of microwells of the upper sub-chip and a large number of microwells of the lower sub-chip to be accurately aligned at the initial position to ensure the smooth addition of droplets to the microwells.

The shortcomings of the prior art mainly include: In order to generate droplets with good uniformity in size, the method of flow-generated-microdroplet requires precise control of the flow rate of two kinds of immiscible liquids. This process usually requires equipment of fluid pumps and other instruments, leading to a more complex instrument system. While the instrument takes quite a large volume, the system is also more expensive. Moreover, the uniformity of droplets is very important to the accuracy and reliability of the analysis results of digital PCR, etc. Not least, in order to ensure that there is no cross-contamination between the generated droplets (the transfer of material molecules between the droplets) and avoid the fusion between droplets (two or more droplets contact each other and become a larger droplet), surfactant is usually needed. Surfactants are usually expensive and affect biochemical reactions in aque-ous solutions. QuantStudio 3D digital PCR system requires many manual operation steps, the process of generating droplets is more complicated, and it splits the aqueous solution in the microwells through the organic phase (oil phase), which is easy to produce cross-contamination between the microwells. On the other hand, the microfluidic chip controlled by the microvalve, which is studied by Stephen Quake, also requires a complex pressure control system (to control the microvalve). In addition, finished cost of the chip, which is a consumable, is expensive. SlipChip requires a large number of microwells of the upper sub-chip and those of the lower sub-chip to be accurately aligned at the initial position to ensure that the droplets are smoothly added to the microwells. It is also demanding for the processing, assembly and control of the chips.

Therefore, those skilled in the art are committed to developing a method for generating a droplet array on a microfluidic chip. The droplet array can be effectively and controllably formed by a simple combination of upper and lower chips and a simple operation method, and the cross-contamination can be effectively and fully avoided by physi-cal isolation without difficulty.

SUMMARY OF INVENTION

In view of the above-mentioned defects of the prior art, the technical problem to be solved by the present invention is how to provide a method for generating a droplet array on a microfluidic chip, which can effectively and controllably form a droplet array through a simple combination of upper and lower chips and a simple operation method, and avoid cross-contamination phenomenon effectively and fully through physical isolation without difficulty, thus overcoming the shortcomings of the prior art.

In the first aspect of the present invention, it provides a method for generating a droplet array on a microfluidic chip, which comprises the following steps:

Step 1. Assembling the upper chip and the lower chip to the initial position, the fluid tube of the upper chip is partially or fully covered by the microwell arrays of the lower chip, and the fluid tube of the upper chip is a structure containing one or more connected fluid channels;

Step 2. Injecting the solution into the chip, and the solution partially or completely fills the microwell array of the lower chip;

Step 3. Moving the upper chip and the lower chip relatively to the liquid splitting position, the fluid tube of the upper chip and the microwell array of the lower chip no longer overlap, and the solution is dispersed into the microwell array to form a droplet array.

Preferably, the microfluidic chip includes the upper chip and the lower chip, wherein the lower surface of the upper chip and the upper surface of the lower chip are in contact with each other, and the lower surface of the upper chip and the upper surface of the lower chip that are in contact with each other need hydrophobic modification treatment; the upper chip or the lower chip is provided with a liquid inlet hole, and the upper chip or the lower chip may also be provided with a liquid outlet hole.

Preferably, the properties of the fluid channel of the upper chip may be linear, curved or a combination of both.

Preferably, the size specifications of the fluid channel of said upper chip range from 1 μm to 10 cm in width, 100 μm to 100 cm in length, and 1 μm to 1 cm in depth.

Preferably, the surface of the fluid channel of the upper chip needs to be hydrophobized or hydrophilic modified.

Preferably, the microwell array of the lower chip may include one or more microwells, and the size and depth of the microwells may be designed to be consistent or different; the surface of the microwells needs to be surface modified, and the surface modification may be selected from one or more of physical modification, chemical modification, and biological modification.

Preferably, after the upper chip and the lower chip are assembled to the initial position in the step 1, an organic phase may be first injected into the chip, and the organic phase comprises a surface chemical component of the hydrophobization modification treatment.

Preferably, the material of the upper chip and the lower chip may be any one of glass, quartz, plastic, ceramic and paper materials.

Preferably, the upper chip and the lower chip can be prepared by photolithography, wet etching with hydrofluoric acid, dry etching, and hot embossing.

Preferably, one or more expansion channel(s) may be designed on the upper chip, the expansion channels may be filled with air or an organic phase, and when the upper chip and the lower chip move relatively to the liquid splitting position, the expansion channels overlap with the microwell array of the lower chip.

In a second aspect of the present invention, it provides a microfluidic chip for generating a droplet array, and the chip comprises:

The upper chip, the fluid tube of the upper chip is a structure containing one or more connected fluid channels;

The lower chip which is provided with microwell array(s);

Wherein, when the upper chip and the lower chip are assembled to the initial position, the fluid tube of the upper chip partially or completely covers the microwell array of the lower chip;

And, when the solution is injected into the chip, the solution is partially or completely filled with the microwell array of the lower chip; and then the upper chip and the lower chip are relatively moved to the liquid splitting position, the fluid tube of the upper chip and the microwell array of the lower chip no longer overlap, so that the solution is dispersed into the microwell array to form a droplet array.

In another preferred embodiment, the lower surface of the upper chip and the upper surface of the lower chip are in contact with each other.

In another preferred embodiment, the lower surface of the upper chip and the upper surface of the lower chip, which are in contact with each other, are hydrophobically modified.

In another preferred embodiment, the upper chip or the lower chip is provided with a liquid inlet hole, and the upper chip or the lower chip may also be provided with a liquid outlet hole.

In another preferred embodiment, the properties of the fluid channel of the upper chip are linear, curved or a combination of both.

In another preferred embodiment, the size of the fluid channel of the upper chip ranges from 1 μm to 10 cm in width, 100 μm to 100 cm in length and 1 μm to 1 cm in depth.

In another preferred embodiment, the surface of the fluid channel of the upper chip is hydrophobic ally or hydrophilic ally modified.

In another preferred embodiment, the microwell array of the lower chip may comprise a plurality of microwells.

In another preferred embodiment, the surface of the microwells is surface-modified.

In another preferred embodiment, the surface modification treatment may be selected from one or more of physical modification, chemical modification, and biological modification.

In another preferred embodiment, the materials of the upper chip and the lower chip are selected from the following group: glass, quartz, plastic, ceramic, paper material, or a combination thereof.

In another preferred embodiment, the materials of the upper chip and the lower chip are selected from the following group: glass, quartz, plastic, ceramic, or a combination thereof.

In another preferred embodiment, the upper chip and the lower chip are prepared by photolithography, wet etching with hydrofluoric acid, dry etching, hot embossing, dry etching, hot embossing, injection molding and 3D printing.

In another preferred embodiment, one or more expansion channels are provided on the upper chip, the expansion channels are filled with air or an organic phase, and when the upper chip and the lower chip move relatively to the liquid splitting position, the expansion channels overlap with the microwell array of the lower chip.

In another preferred embodiment, in the microwell array, the microwell density is 4-100000 wells/cm$^2$, preferably 9-9000 wells/cm$^2$, more preferably 25-5000 wells/cm$^2$ or 100-5000 wells/cm$^2$.

In another preferred embodiment, the volume of each microwell is 0.001-100 nanoliters, preferably 0.01-50 nanoliters, more preferably 0.05-10 nanoliters, and most preferably 0.1-5 nanoliters.

In another preferred embodiment, the ratio of the depth D of each microwell to the cross-sectional area $S^{1/2}$ ($D/S^{1/2}$) is $\frac{1}{200}$ to 1, preferably $\frac{1}{20}$-0.8, more preferably $\frac{1}{5}$-0.5.

In another preferred embodiment, when the cross-section of the microwells is square, the ratio of the depth D to the length A of the square (D/A) of each microwell is $\frac{1}{200}$ to 1, preferably $\frac{1}{20}$-0.8, more preferably $\frac{1}{5}$-0.5.

In another preferred embodiment, the depth D of the microwells is 5-200 microns, preferably 10-100 microns, more preferably 20-50 microns.

In another preferred embodiment, when the cross-section of the microwells is circular, the ratio of the depth D to the length d of the circular shape (D/d) of each microwell is $\frac{1}{200}$ to 1, preferably $\frac{1}{20}$-0.8, more preferably $\frac{1}{5}$-0.5.

It should be understood that within the scope of the present invention, the above-mentioned technical features of the present invention and the technical features specifically described in the following (such as embodiments) can be combined with each other to form a new or preferred technical solution. Limited to space, I will not repeat them here.

Compared with the prior art, the present invention has at least the following technical effects:

(1) Compared with the traditional method of slip chip, the present invention does not need to overlap the part of the microwells of the upper chip and the lower chip to establish a connected fluid channel, which is simpler for chip processing, and greater tolerances is allowed, and no precise alignment operation is required in chip assembly, thus making assembly more convenient;

(2) The present invention does not require a complex control system compared to other droplet generation methods, and can effectively control the size, shape, etc. of the generated droplet;

(3) Compared with the traditional microwell array microfluidic chip, the present invention can perform a good physical isolation, so that there is no cross-contamination between microwells.

The spirit, specific structure and technical effects of the present invention will be further described with reference to the accompanying drawings, so as to fully understand the objects, features and effects of the present invention.

DRAWINGS

EMBODIMENTS

Figure 1:
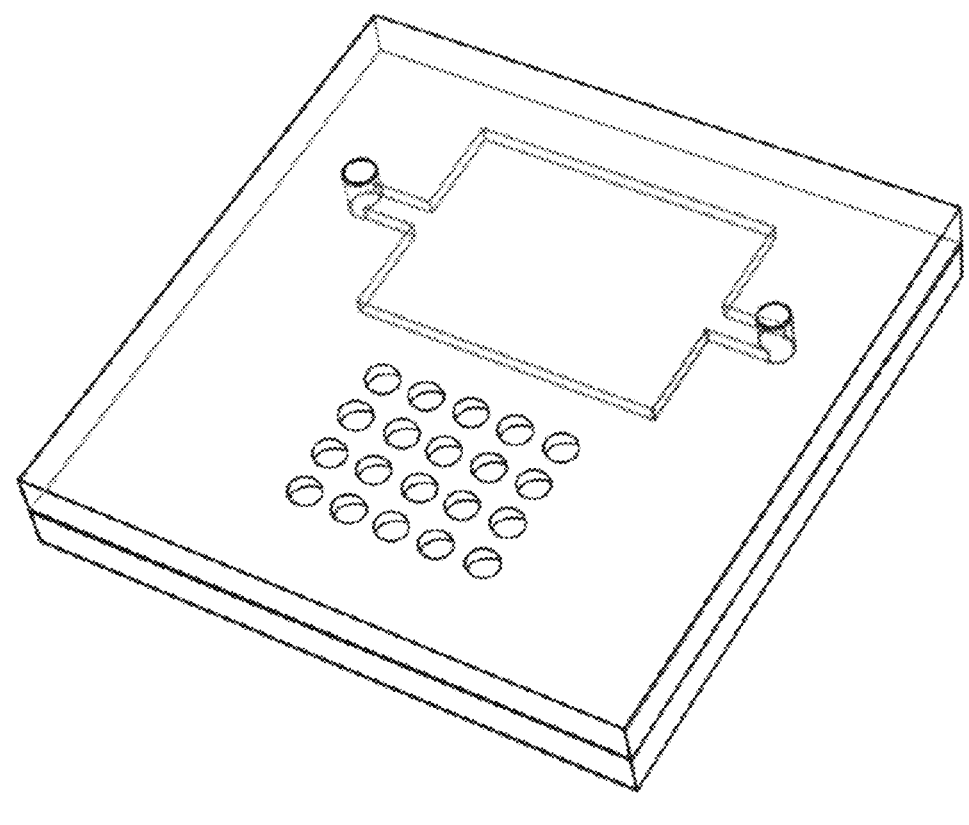
FIG. 1 is a diagram of the upper and lower chips in assembled-position after moving according to a preferred embodiment of the present invention.

After extensive and intensive research and numerous screening and trials, the inventor, for the first time, has developed a displacement microfluidic chip with unique structure. The displacement microfluidic chip of the present invention can quickly, efficiently and easily disperse the solution injected into the chip (e.g., reaction solution for digital PCR) into the microwell array of the lower chip to form a droplet array by sliding the upper chip and the lower chip relative to each other, i.e., when sliding from the initial position to the liquid splitting position. The present invention is completed on such basis.

Terms

As used herein, the terms "upper chip" and "upper chip board" are used interchangeably.

As used herein, the terms "lower chip" and "lower chip board" are used interchangeably.

It should be understood that for ease of description, "up", "down", "left", and "right" are relative and they are used to express relative spatial positional relationships. For example, the upper chip can also be called the lower chip, and the lower chip can also be called the upper chip.

As used herein, the term "between", when used in the context of moving between a "first position" and a "second position," may refer to moving from the first position to the second position only, from the second position to the first position only, or from the first position to the second position and from the second position to the first position. Typically, the first position is the initial position where the upper and lower chips are assembled, or the injection position where the upper and lower chips are located when a fluid (such as a solution) is injected into the chip; the second position is the fluid splitting position.

Microfluidic Chip

As used herein, the terms "chip of the present invention", "microfluidic chip of the present invention", "displacement microfluidic chip", and "displacement microfluidic chip of the present invention" can be used interchangeably, all of which refer to the microfluidic chip described in the second aspect of the present invention. The displacement microfluidic chip of the present invention can quickly, efficiently and easily disperse the solution injected into the chip (e.g., reaction solution for digital PCR) into the microwell array of the lower chip to form a droplet array by sliding the upper chip and the lower chip relative to each other, i.e., when sliding from the initial position to the liquid splitting position.

The displacement microfluidic chip of the invention comprises an "upper chip" and a "lower chip" used in conjunction with each other".

In the present invention, the upper chip includes one or more connected fluid channels, and the size specification of the fluid channels ranges from 1 μm to 10 cm in width, 100 μm to 100 cm in length, and 1 μm to 1 cm in depth.

The microfluidic chip of the present invention can be used to generate droplet arrays of different sizes and shapes.

In another preferred embodiment, the upper chip is provided with a liquid inlet hole.

In another preferred embodiment, the upper chip may be provided with a liquid outlet hole.

In another preferred embodiment, one or more expansion channels are provided on the upper chip, and the expansion channels are filled with air or organic phase. The solution in the upper expansion channel of the chip can be used as an additional reaction solution to improve the overall reaction solution volume, thereby achieving the purpose of improving the reaction sensitivity. In the present invention, the lower chip is provided with a microwell array. In the present invention, the microwell density is not particularly limited. Typically, the microwell density is 4-100,000 holes/cm², preferably 9-9000 holes/cm², more preferably 25-5000 holes/cm² or 100-5000 holes/cm².

The size and depth of the microwells can be designed to be consistent or different.

In the present invention, the lower chip may contain microwells of different sizes for generating liquid cells of different volumes.

In another preferred embodiment, the lower chip may also include microwells with different depths to generate liquid cells with different depths.

In another preferred embodiment, the lower chip may also include micropits of different shapes, and representative shapes include (but are not limited to) a circle, a rectangle, a square, a cross, a triangle, or any other shape.

In the present invention, the surface of the microwells may be surface-modified or not surface-modified. Representative surface modification treatments include (but are not limited to) physical modification, chemical modification, biological modification, or combinations thereof.

Preferably, the surface of the chip of the present invention is modified by method of gaseous silanization, for example, the surface of the glass is subjected to a hydrophobic modification treatment using dimethyldichlorosilane.

Method for Generating Droplet Array

The invention also provides a method for generating a droplet array based on the displacement microfluidic chip of the invention.

Typically, the method includes:

Step 1. the displacement microfluidic chip of the present invention is provided, wherein the upper chip and the lower chip are in the initial position; the fluid tube of the upper chip partially or completely covers the microwell array of the lower chip;

Step 2. injecting the solution into the chip so that the solution partially or completely fills the microwell array of the lower chip;

Step 3. moving (or sliding) the upper chip and the lower chip relatively to the liquid splitting position, the fluid tube of the upper chip and the microwell array of the lower chip no longer overlap, and the solution is dispersed into the microwell array to form a droplet array.

Preferably, when the displacement microfluidic chip of the present invention is provided with an expansion channel, and the expansion channel contains an organic phase, the representative organic phase is a mixture of mineral oil and tetradecane of equal volume, for example. When a layer of organic phase liquid is added between the upper and lower chips and they are assembled at the initial position for sampling, the connected fluid channels of the upper chip and the microwells of the lower chip are occupied by the organic phase.

Application

The present invention also provides the application of the displacement microfluidic chip of the invention and the generation of the droplet array.

With the microfluidic chip of the present invention, an array containing a large number of microdroplets (e.g. 1000-10000 or more microdroplets) can be effectively and controllably formed by simple operation of the upper chip and the lower chip.

The apparatus and method of the present invention can be applied to applications requiring a large number of independent micro-liquids. A typical application is to use the displacement microfluidic chip of the present invention for digital PCR reaction to quantitatively detect nucleic acid samples.

The main advantages of the invention include:

(a) The droplet array can be effectively and controllably formed by a simple combination of upper and lower chips and a simple operation method, and the cross-contamination can be effectively and fully avoided by physical isolation without difficulty.

(b) The present invention does not need to overlap the part of the microwells of the upper chip and the lower chip to establish a connected fluid channel, which is simpler for chip processing, and greater tolerances is allowed, and no precise alignment operation is required in chip assembly, thus making assembly more convenient.

(c) The present invention does not require a complex control system compared to other droplet generation methods, and can effectively control the size, shape, etc. of the generated droplet.

The present invention is preferrably described below in conjunction with specific embodiments. It should be understood that these examples are intended to illustrate the invention only and not to limit the scope of the invention. The following embodiments do not specify the specific conditions of the experimental method, usually according to the conventional conditions, or according to the conditions recommended by the manufacturer. Unless otherwise stated, percentages and parts are weight percentages and parts by weight.

Embodiment 1. Preparation of Displacement Microfluidic Chip No. 1 and Generation of a Droplet Array of Uniform Size In this embodiment, the upper chip (shown in FIG. 3) and the lower chip (shown in FIG. 4) are prepared on the glass material by wet etching method. The fluid channel of the upper chip has a width of 5 mm, a length of 15 mm, and a depth of 50 microns. The upper chip contains a liquid inlet and a liquid outlet.

Figure 3:
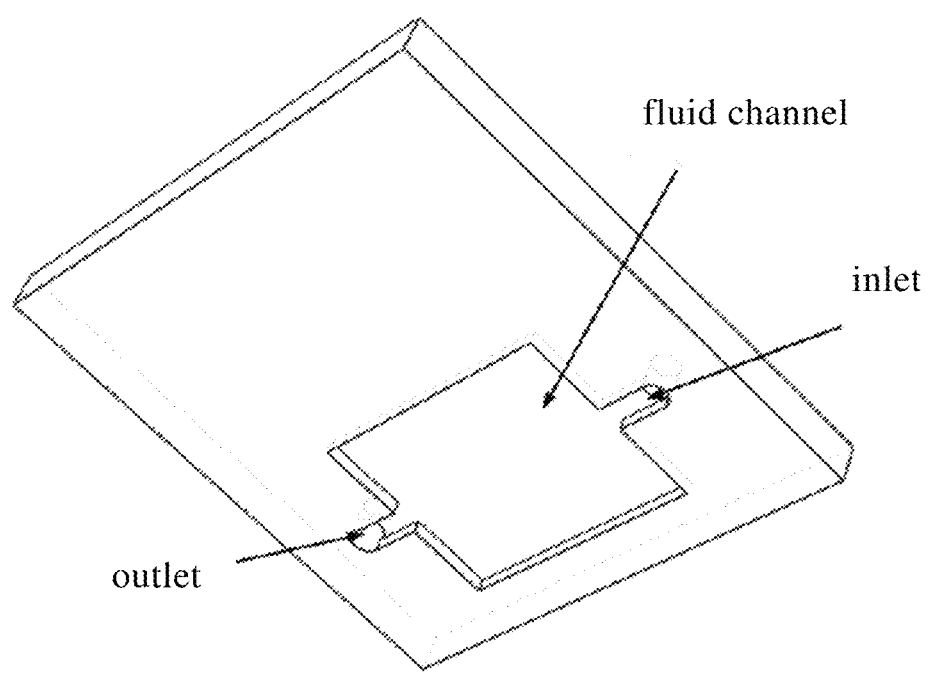
FIG. 3 is a diagram of bottom view of an upper chip according to a preferred embodiment of the present invention.
Figure 4:
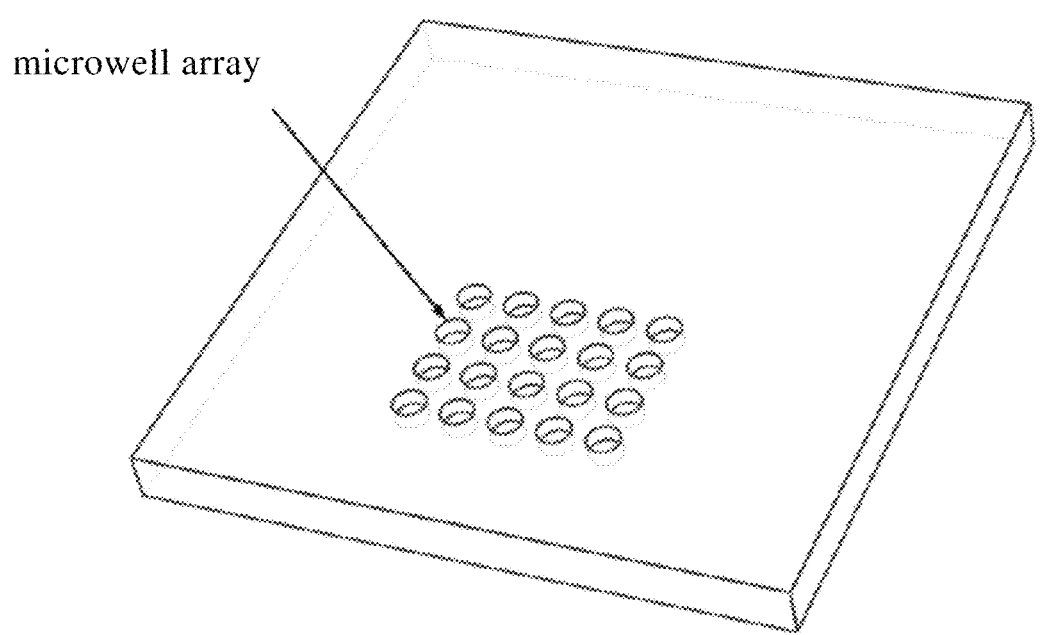
FIG. 4 is a diagram of top view of a lower chip of a preferred embodiment of the present invention.

To show the structural features more conveniently, the schematic structure of this microfluidic chip is shown in FIG. 3 and FIG. 4. However, the manufactured lower chip actually contains 5000 microwells distributed in an area 4.5 mm wide and 12.5 mm long. The diameter of the lower chip after etching is 80 microns and the depth is 25 microns.

The surface of the chip undergoes gaseous silanization, and the surface of the glass is subjected to a hydrophobic modification treatment using dimethyldichlorosilane. Organic phases are split into mineral oil and tetradecane mixed in equal volume.

Figure 2:
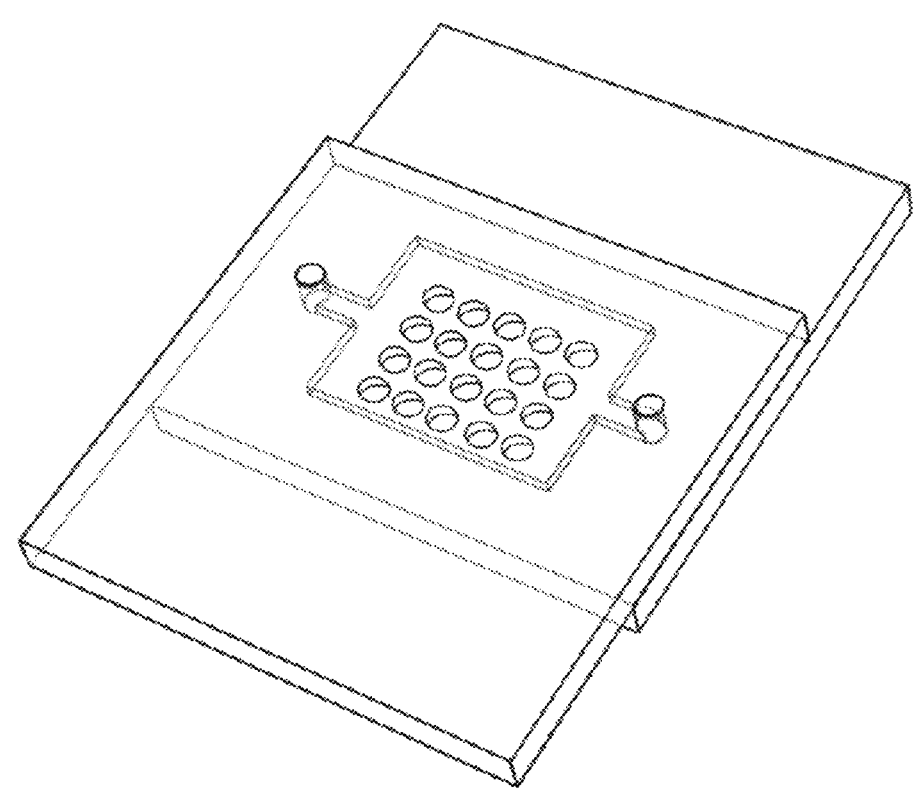
FIG. 2 is a diagram of the initial position of the upper and lower chips in assembled-position according to a preferred embodiment of the present invention.

After the upper chip and the lower chip are assembled, a layer of organic phase liquid is added in the middle of the upper and lower chips, and the relative positions of the two are placed in the initial position for sampling as shown in FIG. 2, and the fluid channels of the upper chip and the microwells of the lower chip are occupied by the organic phase. Through the inlet of the upper chip, an aqueous solution containing polyethylene glycol octylphenyl ether and fluorescein is injected into the chip. The aqueous solution displaces the organic phase in the fluid channels and microwells.

By manually shifting the relative positions, the fluid channels of the upper chip are staggered with the microwell array of the lower chip to the fluid splitting position as shown in FIG. 1, and the fluid in the microwell array of the lower chip forms a microdroplet microwell array.

The droplets in the microwells were photographed by fluorescence microscope (Nikon Ti-2) and the size of the droplets was analyzed by Nikon's analysis software. The average diameter of the generated droplets is 74 microns, and their standard deviation is less than 5% (about 100 droplet measurements). This proves that the method proposed by the present invention can be used to generate a droplet array of uniform size.

Embodiment 2. Digital PCR Experiment

The chip preparation is the same as that of Embodiment 1. The upper chip and the lower chip are prepared on the glass material by wet etching. The fluid channel of the upper chip has a width of 5 mm, a length of 15 mm, and a depth of 50 microns. The upper chip contains a liquid inlet and a liquid outlet. The lower chip contains 5000 microwells distributed in an area 4.5 mm wide and 12.5 long. The diameter of the lower chip after etching is 80 microns and the depth is 25 microns. The surface of the chip undergoes gaseous silanization, and the surface of the glass is subjected to a hydrophobic modification treatment using dimethyldichlorosilane. Organic phases are divided into mineral oil and tetradecane mixed in equal volume. When a layer of organic phase liquid is added between the upper and lower chips and they are assembled at the initial position for sample adding, the connected fluid channels of the upper chip and the microwells of the lower chip are occupied by the organic phase.

Preparation of PCR reaction solution: 50 microliters of reaction reagent including: primer-1: CAGCGAGTCAGT-GAGCGAGGAA (SEQ ID No: 1) 1.25 microliters; primer-2: TGTAAAGCCTGGGGTGCCTAA (SEQ ID No: 2) 1.25 microliters; EvaGreen 2×PCR reaction solution (purchased from Bole Company) 25 microliters; PCR reagent water 15 microliters; 10 mg/mL bovine serum albumin (BSA) 2.5 microliters, sample plasmid: Tet-pLKO-puro 5 microliters.

After the PCR reaction solution is injected into the chip, the fluid channel of the upper chip and the microwell array of the lower chip are staggered by manual shifting of their relative position, and the liquid in the microwell array of the lower chip forms the microdroplet microwell array of PCR solution. The chip was placed on a flat-panel PCR instrument, and the amplification temperature was set at 95° C. for 1 minute, 55° C. for 30 seconds, 72° C. for 30 seconds, and repeated 40 cycles.

Figure 5:
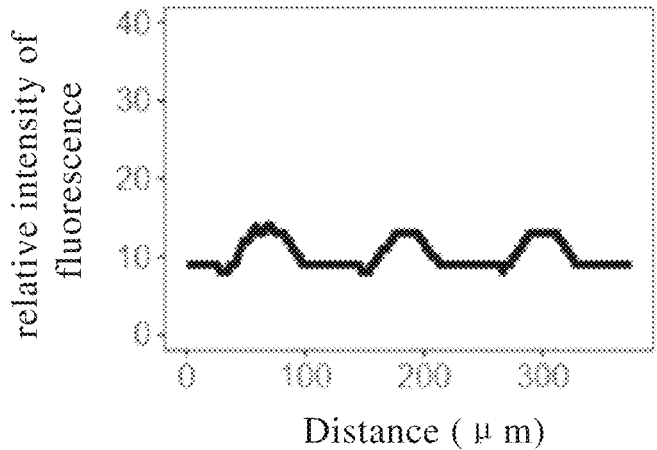
FIG. 5 is a fluorescence signal diagram of three adjacent microwells before digital PCR amplification according to a preferable embodiment of the present invention.
Figure 6:
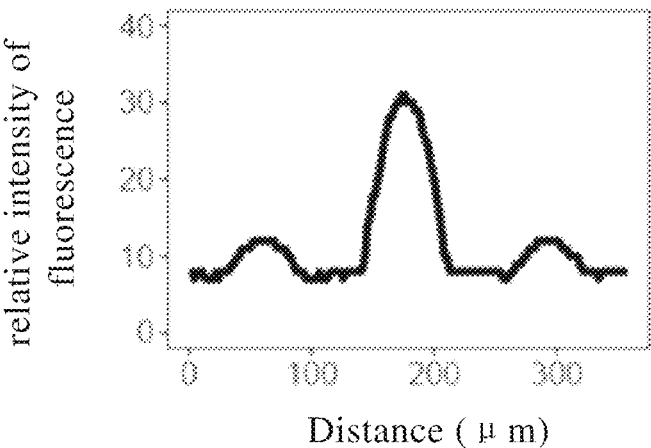
FIG. 6 is a fluorescence signal diagram of three adjacent microwells after digital PCR amplification according to a preferable embodiment of the present invention.

After the thermal cycle is completed, the chip is placed on an inverted fluorescence microscope (Nikon Ti-2) for photographing and fluorescence measurement. The fluorescence detection signal of FAM channel is used to determine whether gene amplification happens. If the microwells contain target gene fragments, there will be significant fluorescence enhancement after thermal cycling. The experimental data were analyzed for the changes in fluorescence signal before (as shown in FIG. 5) and after (as shown in FIG. 6) the measurement of three adjacent microwells, and it could be found that the signal peak of one of the microwells was significantly enhanced, while the other two remained basically unchanged, indicating that one of the microwells contained the target gene fragment and underwent PCR amplification, while the other two microwells did not contain the target gene fragment, so there was no change after PCR amplification. This demonstrates that the method of the present invention can ensure that each microwell contains at most one target gene fragment and that cross-contamination between microwells is less likely to occur, providing a basis for the accuracy of quantitative assays such as digital PCR.

Figure 7:
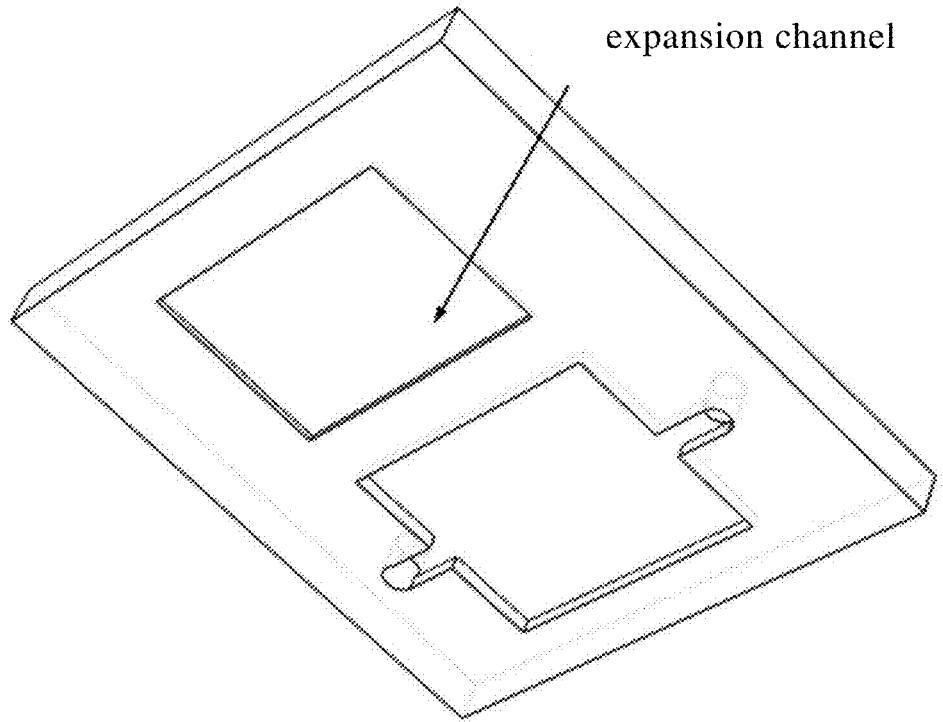
FIG. 7 is a schematic diagram of an upper chip with an extended channel according to a preferred embodiment of the present invention.
Figure 8:
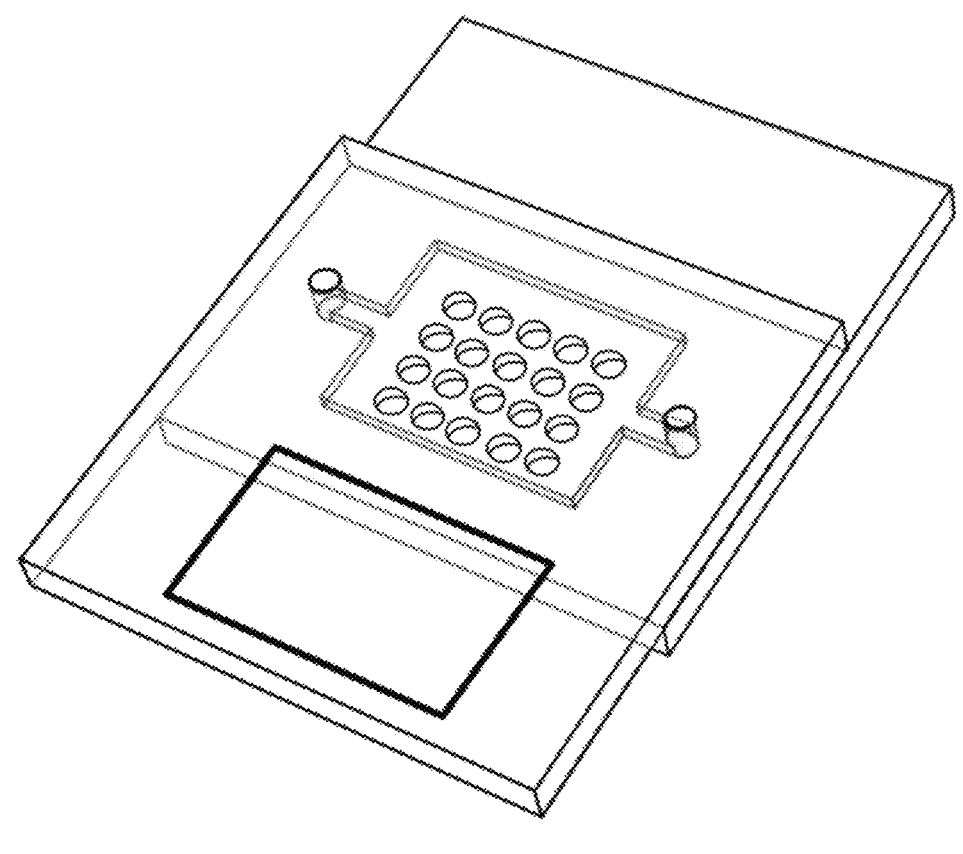
FIG. 8 is the assembled-position of the upper chip and the lower chip with the expansion channel in initial position according to a preferred embodiment of the present invention.
Figure 9:
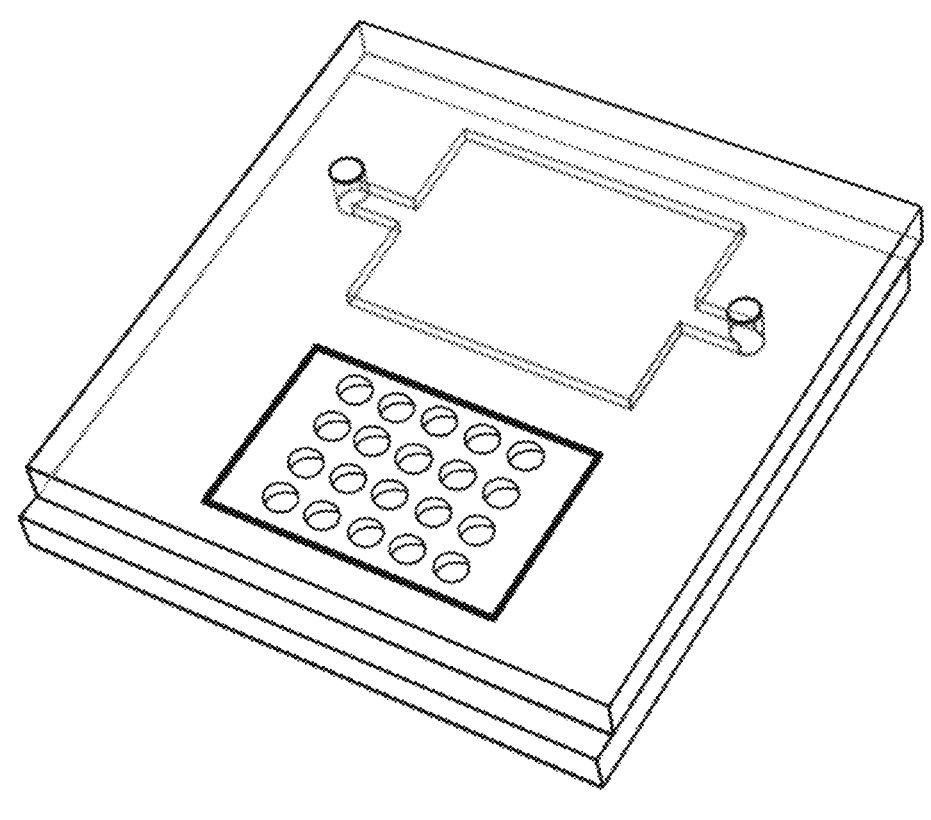
FIG. 9 is a diagram of the upper and the lower chips with the expansion channel after moving according to a preferred embodiment of the present invention.

The method provided by the invention can also design an expansion channel on the upper chip (as shown in FIG. 7). The expansion channel may be the same depth as the fluid channel, shallower or deeper; the width may also be the same as or different from the fluid channel. The expansion channel can be filled with air or organic phase liquid. After the upper chip with the expansion channel and the lower chipset are assembled in the initial position shown in FIG. 8, an aqueous solution is injected to partially or completely fill the microwells of the lower chip. After that, the upper chip and the lower chip are moved relative to the liquid splitting position shown in FIG. 9, the droplet array is formed, and the droplets are physically isolated, and the expansion channel is overlapped with the microwell array of the lower chip, which provides additional expansion space for the aqueous solution in the microwells. In some processes with temperature changes, such as temperature rise, the aqueous solution will expand, the expansion channel provides space for the expansion of the aqueous solution, further ensuring that there is no cross-contamination between the microwells during the reaction.

Embodiment 3, Displacement Microfluidic Chip No. 2

Figure 10:
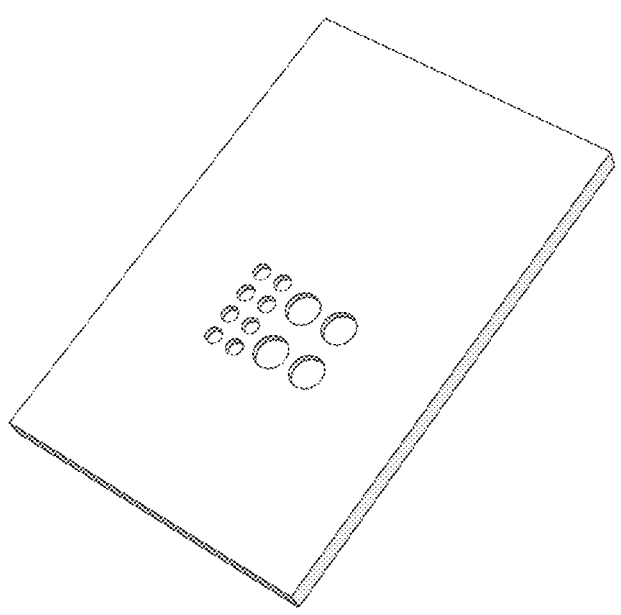
FIG. 10 is a top view of a lower chip according to another preferred embodiment of the present invention, in which microwells of different sizes are provided.
Figure 11:
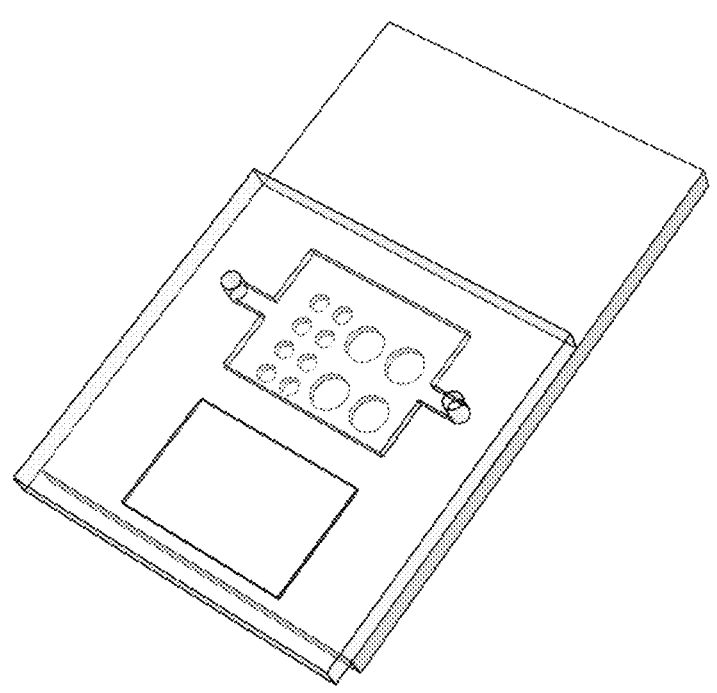
FIG. 11 is a diagram of the initial position of the upper chip and the lower chip with the expansion channel in assembled-position according to another preferred embodiment of the present invention.
Figure 12:
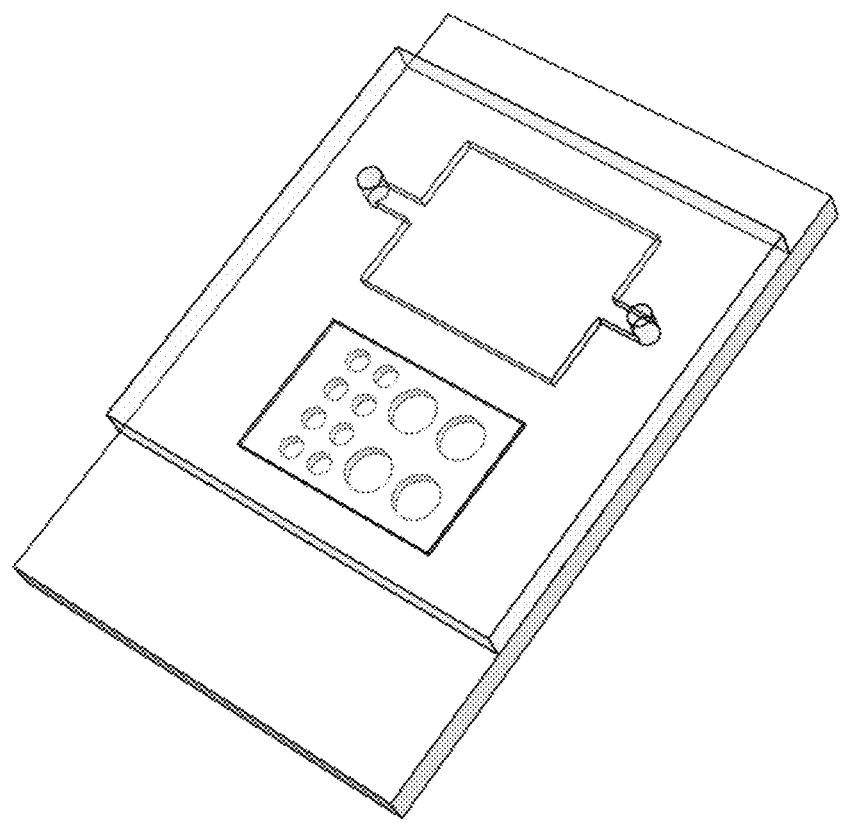
FIG. 12 is the assembled position of the upper and the lower chips with the expansion channel after moving according to another preferred embodiment of the present invention.

See FIGS. 10, 11 and 12. In this embodiment, the structure of the upper chip is the same as that in Embodiment 1, and the difference lies in that: the lower chip is provided with a microwell array with gradually increasing diameter, including: 4000 microwells are split into four columns with each column 1000 microwells, and the microwell diameter is: 60 microns, 100 microns, 250 microns, 500 microns from the left column to the right, and the depth is 25 microns.

The chip preparation may be the same as in Embodiment 1. The upper chip and the lower chip are prepared on the glass material by wet etching.

In this embodiment, the fluid channel of the upper chip has a width of 10 mm, a length of 25 mm and a depth of 50 μm. The upper chip contains a liquid inlet and a liquid outlet.

In the lower chip in this embodiment, the volume of each irregular-shaped microwell is 0.01-100 nanoliters. The microwells are distributed in an area of 4.5 mm wide and 12.5 mm long.

The depth-to-width ratio (depth/width) of the micropits after micropit etching of the lower chip is preferably less than 1, more preferably ≤½.

Embodiment 4, Displacement Microfluidic Chip No. 3

Figure 13:
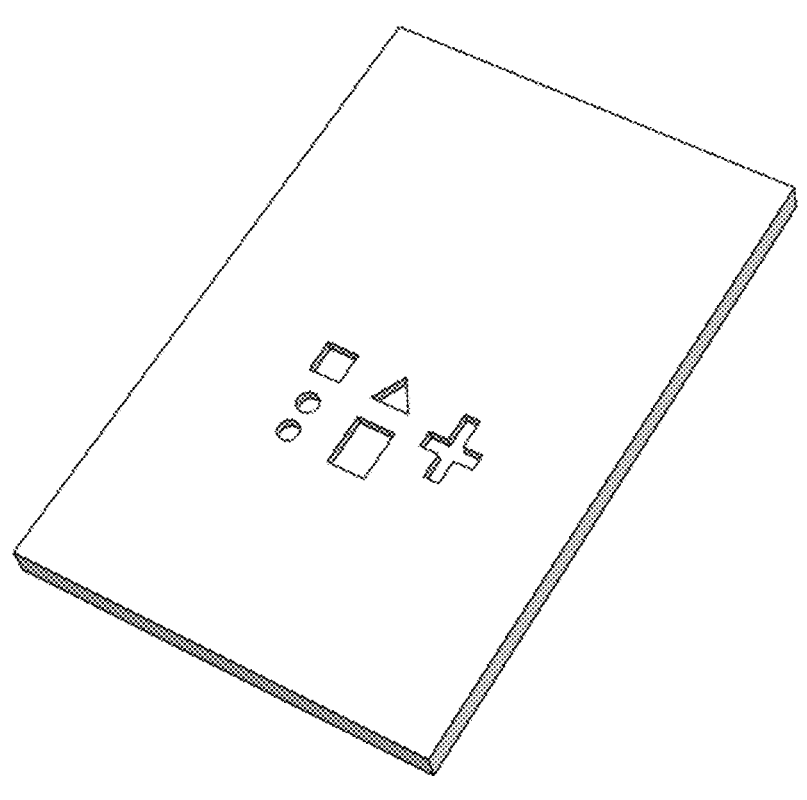
FIG. 13 is a diagram of top view of a lower chip according to another preferred embodiment of the present invention, in which microwells of different shapes are provided.
Figure 14:
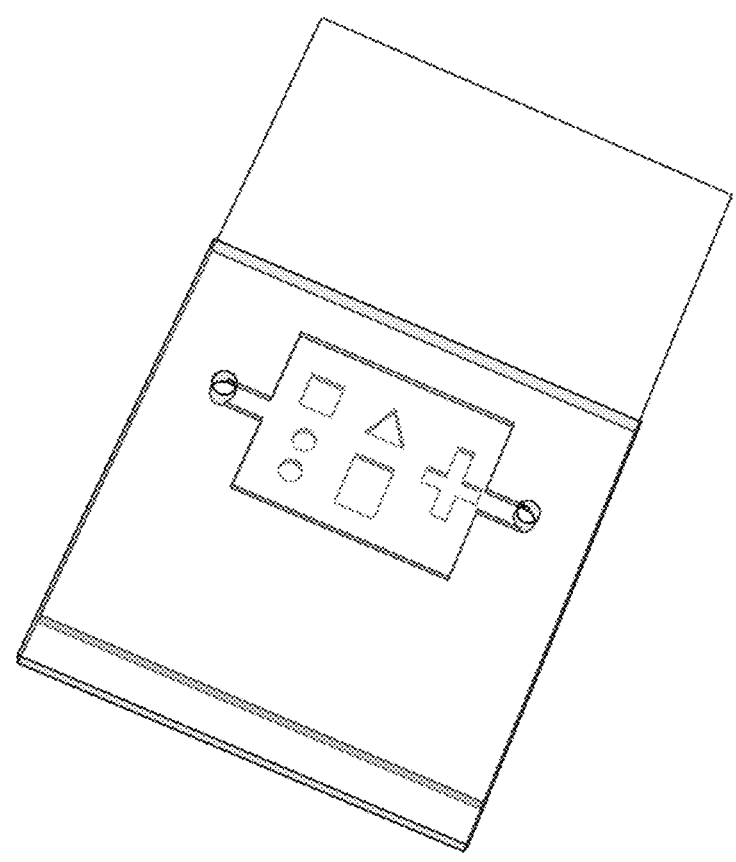
FIG. 14 is a diagram of the initial position of the upper chip with an extended channel and the lower chip shown in FIG. 13 in the assembled position.
Figure 15:
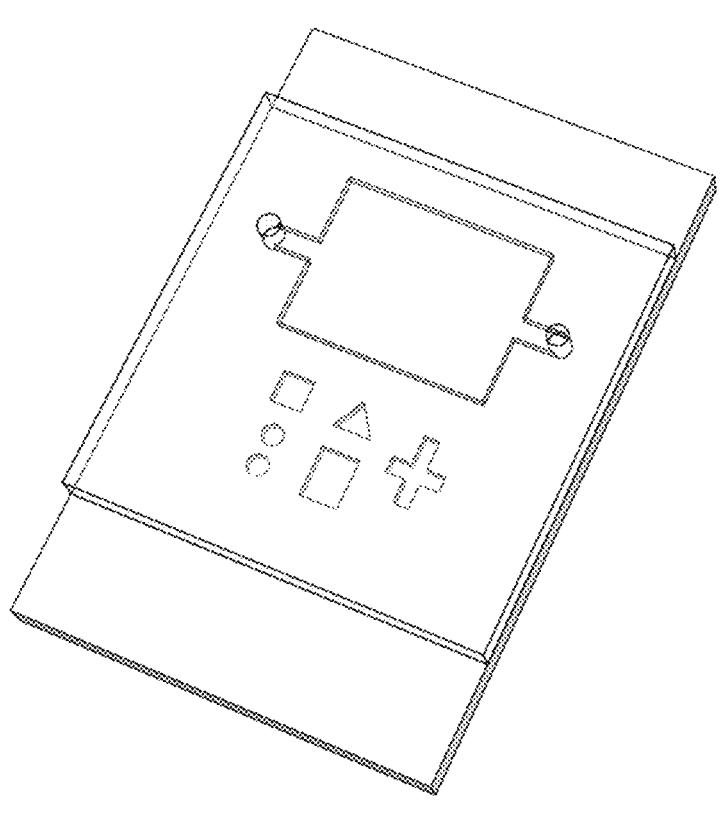
FIG. 15 is the assembled position of the upper chip with the extended channel and the lower chip shown in FIG. 13 in the liquid splitting and assembled position.

See FIGS. 13, 14 and 15. In this embodiment, the structure of the upper chip is the same as that in Embodiment 1, and the difference lies in that: the lower chip is provided with microwell array composed of microwells of irregular shape including: circular, rectangular, square, cross-shaped, triangular.

The chip preparation may be the same as in Embodiment 1. The upper chip and the lower chip are prepared on the glass material by wet etching.

In this embodiment, the fluid channel of the upper chip has a width of 5 mm, a length of 15 mm and a depth of 50 μm. The upper chip contains a liquid inlet and a liquid outlet.

In this embodiment, the volume of each microwell may be 0.1-100 nanoliters or 1-50 nanoliters.

The depth-to-width ratio (depth/width) of the micropits after micropit etching of the lower chip is preferably less than 1.

Embodiment 5, Displacement Microfluidic Chip No. 4

Figure 16:
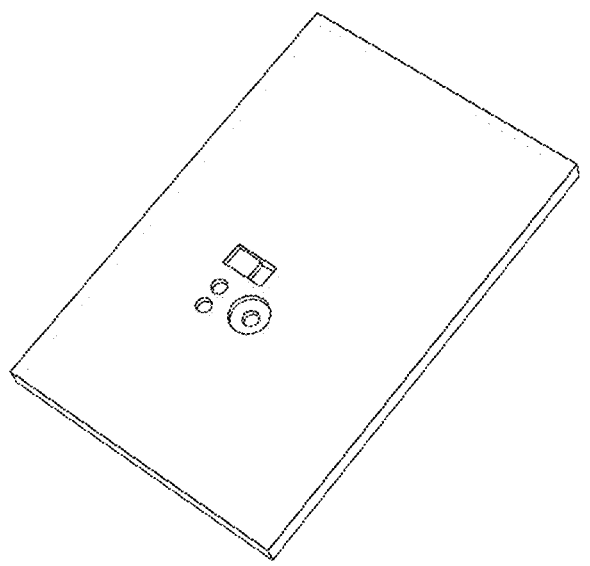
FIG. 16 shows a schematic diagram of a lower chip according to another preferred embodiment of the present invention, in which different microstructures may be provided in one microcell.

See FIG. 16. In this embodiment, the structure of the upper chip is the same as that in Embodiment 1, and the difference lies in that: the microwells with irregular shape on the lower chip include circular holes, stepped circular holes, and stepped square holes. The etched circular holes are 80 microns in diameter and 25 microns in depth; the first stage of the stepped circular holes is 10-1000 microns in diameter and 2-200 microns in depth, and the second stage is 5-500 microns in diameter and 1-100 microns in depth. The stepped square holes are partially through the lower chip, the first stage rectangle is 10-1000 microns in length, 10-1000 microns in width, and 2-200 microns in depth, and the second stage rectangle is 5-500 microns in length, 5-500 microns in width, and 1-100 microns in depth.

The chip preparation may be the same as in Embodiment 1. The upper chip and the lower chip are prepared on the glass material by wet etching.

In this embodiment, the fluid channel of the upper chip has a width of 5 mm, a length of 15 mm and a depth of 50 μm. The upper chip contains a liquid inlet and a liquid outlet.

In the lower chip in this embodiment, the volume of each irregular-shaped microwell is 0.1-100 nanoliters. The microwells are distributed in an area of 5 mm wide and 15 long.

The depth-to-width ratio (depth/width) of the micropits after micropit etching of the lower chip is preferably less than 0.5.

Embodiment 6, Displacement Microfluidic Chip No. 5

In this embodiment, the structure of the upper chip is the same as in Embodiment 1, and the lower chip is provided with an array of microwells of the same diameter, 3000 microwells divided into 10 columns of 300 each, with a microwell diameter of: 250 microns and a depth of 25 microns.

The chip preparation may be the same as in Embodiment 1. The upper chip and the lower chip are prepared on the glass material by wet etching.

Figure 17:
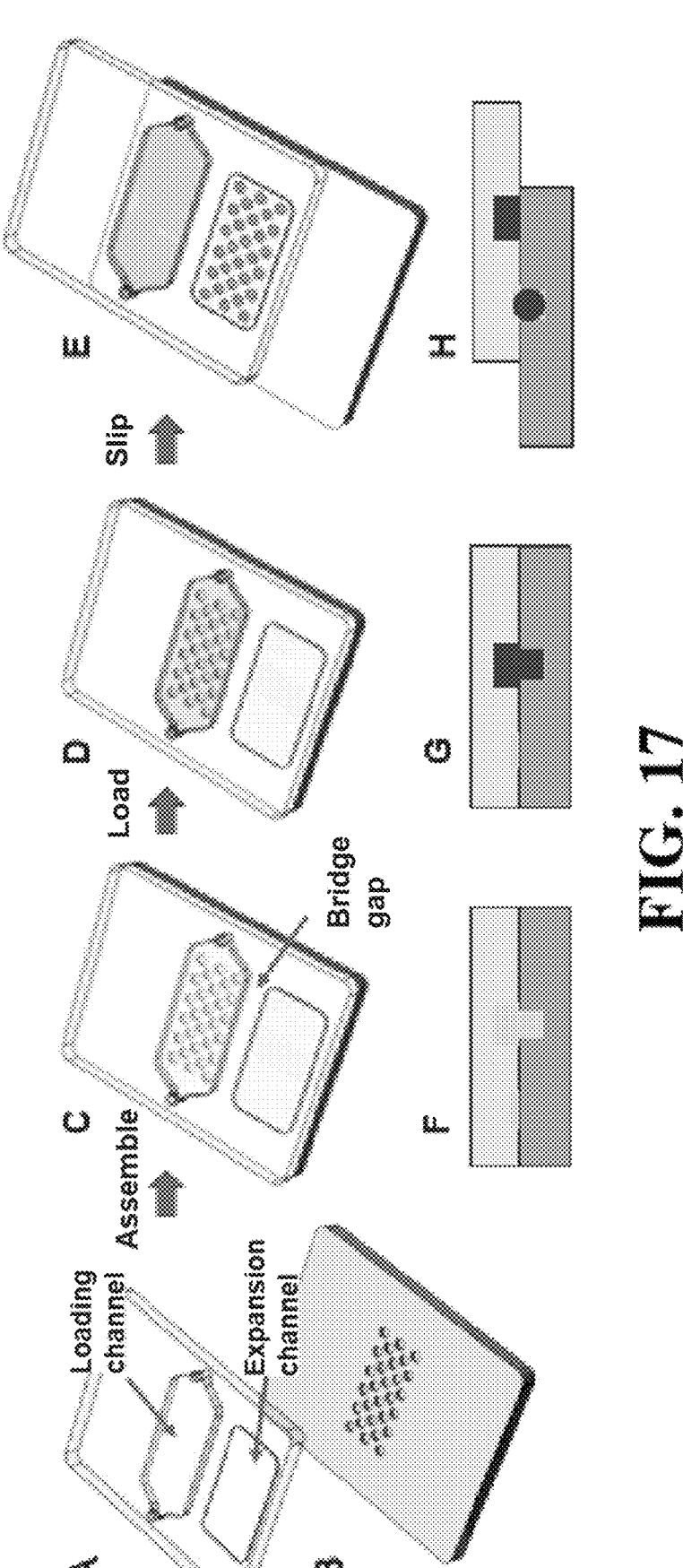
FIG. 17 shows the reaction process after the movement of the upper chip with an extended channel and the lower chip in digital PCR.

Using the microfluidic chip No. 5, the process shown in FIG. 17 is used to generate a droplet array and perform digital PCR detection:

The process includes: assembling the upper chip A and the lower chip B to form a displacement microfluidic chip (C), then sampling (D), sliding to form a droplet array (E), and then incubating and detecting the microfluidic chip. Among them, the cross-sectional view of the microfluidic chip in the corresponding state is given below Figures C, D and E.

Figure 18:
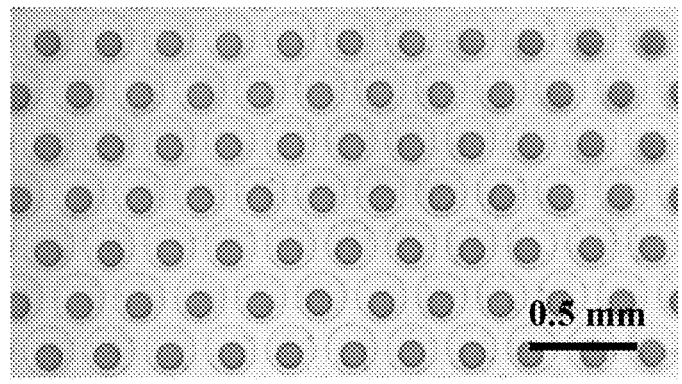
FIG. 18 shows another preferred embodiment of the present invention to generate a uniform size microhole array.

FIG. 18 shows the results of the formation of the droplet array of this embodiment.

Embodiment 7 Application of Digital PCR

In this embodiment the displacement microfluidic chip No. 1 prepared in Embodiment 1 was used and the digital PCR reaction was performed using the same method as in Embodiment 2, and the results of the digital PCR reaction were compared with that of the Naica™ Crystal Microdrop Digital PCR System from Stilla.

After the PCR reaction solution is injected into the chip, the fluid channel of the upper chip and the microwell array of the lower chip are staggered by manual shifting of their relative position, and the liquid in the microwell array of the lower chip forms the microdroplet microwell array of PCR solution. The chip was placed on a flat-panel PCR instrument, and the amplification temperature was set at 95° C. for 1 minute, 55° C. for 30 seconds, 72° C. for 30 seconds, and repeated 40 cycles.

After the thermal cycle is completed, the chip is placed on an inverted fluorescence microscope (Nikon Ti-2) for photographing and fluorescence measurement. The fluorescence detection signal of FAM channel is used to determine whether gene amplification happens. If there is gene amplification, there is obvious fluorescence signal enhancement in the microwells, which is defined as a positive point.

The number of positive points and the number of total microfluidic in the experiment can be calculated by the principle of Poisson distribution statistics. This Embodiment achieved good consistency with Stilla's digital PCR quantification results at 3 different concentrations (10 fg/µl, 1 fg/µl, 0.1 fg/µl) of nucleic acids.

Figure 19:
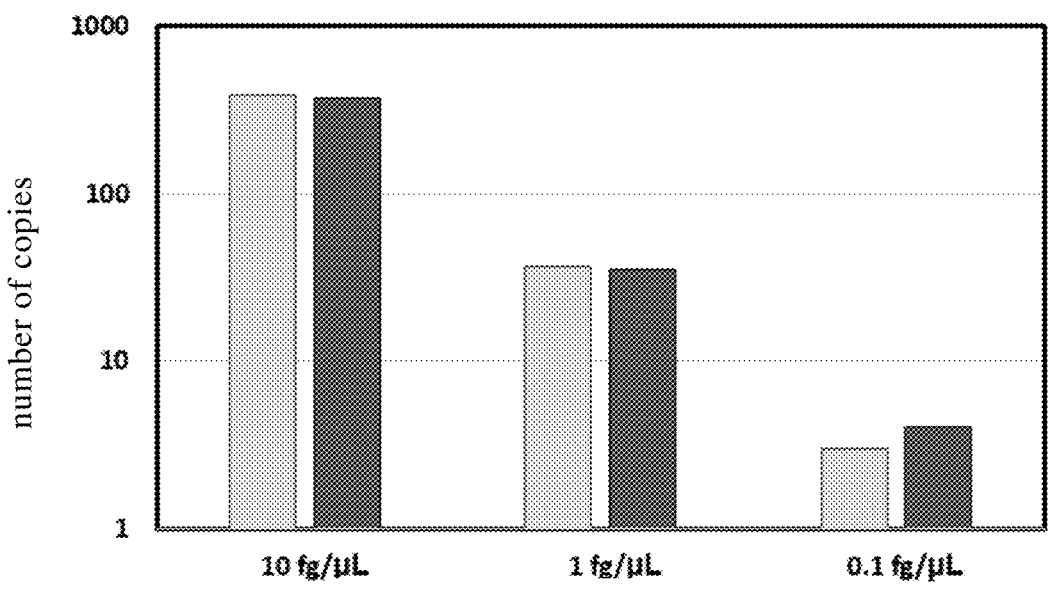
FIG. 19 shows the nucleic acid quantitative detection results obtained using a digital PCR system based on the microfluidic chip of the present invention.

FIG. 19 shows the quantitative results of the digital PCR of this embodiment.

Preferred embodiments of the present invention are described in detail above. It should be understood that the general art in the art can make many modifications and changes according to the concept of the present invention without creative work. Therefore, all technical solutions that can be obtained by those skilled in the art through logical analysis, reasoning or limited experiments on the basis of the prior art according to the spirit of the present invention should be within the protection scope determined by the claims.

14 upper chip and the microwell array of the lower chip no longer overlap, and the solution is dispersed into the microwell array to form the droplet array;

wherein the droplet array is an array containing 1000 or more microdroplets.

2. The method according to claim 1, wherein the microfluidic chip includes the upper chip and the lower chip, and the lower surface of the upper chip and the upper surface of the lower chip that are in contact with each other need hydrophobic modification treatment.

3. The method of claim 1, wherein the one or more connected fluid channels of the upper chip are linear, curved or a combination of both.

---

---

The invention claimed is:

1. A method for generating a droplet array on a microfluidic chip, wherein the microfluidic chip includes an upper chip and a lower chip, wherein a fluid tube of the upper chip is a structure containing a one or more connected fluid channels; and the lower chip is provided with a microwell array;

wherein a lower surface of the upper chip and an upper surface of the lower chip are in contact with each other;

wherein, when the upper chip and the lower chip are assembled to a initial position, the fluid tube of the upper chip completely covers the microwell array of the lower chip;

the upper chip or the lower chip is provided with a liquid inlet hole, and the upper chip or the lower chip may also be provided with a liquid outlet hole;

and the method includes the following steps:

Step 1. Assembling the upper chip and the lower chip to the initial position, the fluid tube of the upper chip completely covers the microwell array of the lower chip, and the fluid tube of the upper chip is the structure containing the one or more connected fluid channels;

Step 2. Injecting solution into the microfluidic chip, and the solution partially or completely fills the microwell array of the lower chip;

Step 3. Moving the upper chip and the lower chip relatively to a liquid splitting position, the fluid tube of the 4. The method of claim 1, wherein a size specifications of the one or more connected fluid channels of said upper chip range from 1 µm to 10 cm in width, 100 µm to 100 cm in length, and 1 µm to 1 cm in depth.

5. The method of claim 1, wherein a surface of the one or more connected fluid channels of the upper chip needs to be hydrophobized or hydrophilic modified.

6. The method of claim 1, wherein the microwell array of the lower chip includes one or more microwells, and a size and depth of the one or more microwells is designed to be consistent or different; a surface of the one or more microwells needs to be surface modified, and the surface modification is selected from one or more of physical modification, chemical modification, and biological modification.

7. The method of claim 1, wherein after the upper chip and the lower chip are assembled to the initial position in the step 1, an organic phase is first injected into the microfluidic chip, wherein the organic phase comprises a surface chemical component of the hydrophobization modification treatment.

8. The method according to claim 1, wherein a material of the upper chip and the lower chip is selected from any one of glass, quartz, plastic, ceramic, and paper materials.

9. The method of claim 1, wherein the upper chip and the lower chip can be prepared by photolithography, wet etching with hydrofluoric acid, dry etching, and hot embossing.

10. The method of claim 1, wherein one or more expansion channels are designed on the upper chip, the one or more expansion channels are filled with air or an organic phase, and when the upper chip and the lower chip move relatively to the liquid splitting position, the one or more expansion channels overlap with the microwell array of the lower chip.

11. The method of claim 1, wherein the droplet array is an array containing 10000 or more microdroplets.

12. The method of claim 1, wherein after the upper chip and the lower chip are assembled to the initial position in the step 1, an organic phase is first injected into the microfluidic chip.

13. The method of claim 12, wherein the organic phase is a mixture of mineral oil and tetradecane of equal volume.

14. The method of claim 1, wherein the microwell array has a microwell density of 25-5000 wells/cm$^2$.

15. The method of claim 1, wherein each microwell of the microwell array has a volume of 0.001-100 nanoliters.

\* \* \* \* \*

SEQUENCE LISTING

<160> NUMBER OF SEQ ID NOS: 2

<210> SEQ ID NO 1
<211> LENGTH: 22
<212> TYPE: DNA
<213> ORGANISM: Artificial Sequence
<220> FEATURE:
<223> OTHER INFORMATION: Primer

<400> SEQUENCE: 1
cagcgagtca gtgagcgagg aa                                          22

<210> SEQ ID NO 2
<211> LENGTH: 21
<212> TYPE: DNA
<213> ORGANISM: Artificial Sequence
<220> FEATURE:
<223> OTHER INFORMATION: Primer

<400> SEQUENCE: 2
tgtaaagcct ggggtgccta a                                          21